(12) United States Patent
Weber

(10) Patent No.: US 7,300,410 B1
(45) Date of Patent: *Nov. 27, 2007

(54) ARM SUPPORT IN SLING, WITH CODED STRAP AND/OR CONNECTIONS

(75) Inventor: James J Weber, Santa Barbara, CA (US)

(73) Assignee: Weber Orthopedic Inc., Santa Paula, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/370,568

(22) Filed: Mar. 9, 2006

Related U.S. Application Data

(63) Continuation-in-part of application No. 10/718,058, filed on Nov. 21, 2003, now Pat. No. 7,189,213.

(51) Int. Cl.
A61F 5/00 (2006.01)
A61F 5/37 (2006.01)

(52) U.S. Cl. .............. 602/4; 602/5; 128/878

(58) Field of Classification Search ............ 434/395, 434/396, 433; 602/4, 5, 15, 20, 62; 128/869, 128/878
See application file for complete search history.

(56) References Cited

U.S. PATENT DOCUMENTS

| | | | |
|---|---|---|---|
| 3,638,334 A * | 2/1972 | Malikowski | 434/260 |
| 4,039,039 A * | 8/1977 | Gottfried | 602/13 |
| 4,683,601 A | 8/1987 | Lagin | |
| 4,841,961 A * | 6/1989 | Burlage et al. | 128/876 |
| 5,000,169 A * | 3/1991 | Swicegood et al. | 602/16 |
| 5,334,132 A * | 8/1994 | Burkhead | 602/4 |
| 5,449,965 A * | 9/1995 | Tsuru | 310/351 |
| 5,566,682 A | 10/1996 | Yavitz | |
| 5,569,172 A * | 10/1996 | Padden et al. | 602/20 |
| 5,738,640 A | 4/1998 | Carlson-Orsi | |
| 6,009,873 A | 1/2000 | Neviaser | |
| D445,506 S | 7/2001 | Vinson et al. | |
| 6,438,779 B1 | 8/2002 | Brown | |
| 6,659,971 B2 * | 12/2003 | Gaylord | 602/4 |
| 6,790,201 B2 * | 9/2004 | Meyer | 604/345 |
| 6,949,077 B2 * | 9/2005 | Froom | 602/21 |
| 2004/0215119 A1 * | 10/2004 | Avon | 602/4 |

* cited by examiner

*Primary Examiner*—Patricia Bianco
*Assistant Examiner*—Kiandra C Lewis
(74) *Attorney, Agent, or Firm*—William W. Haefliger

(57) ABSTRACT

An arm supporting pillow in sling apparatus, comprising in combination a flexible sling, with a first strap having connection to the sling to be supported by a user, an insert pillow received in the sling, to be retrievable from the sling, the sling and pillow dimensioned to receive a user's forearm alongside the pillow, in the sling.

29 Claims, 8 Drawing Sheets

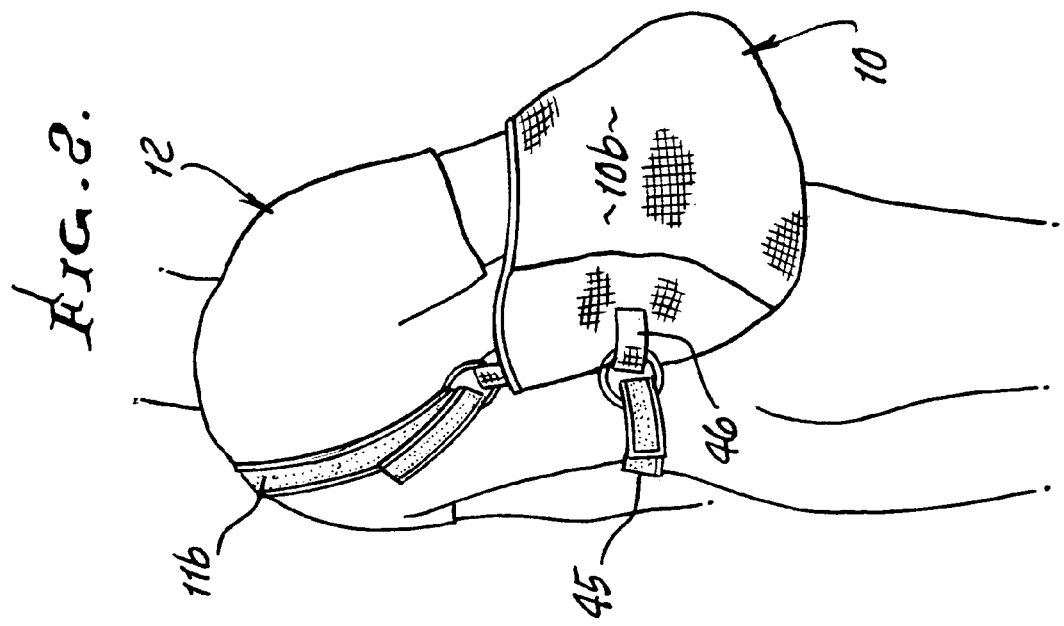
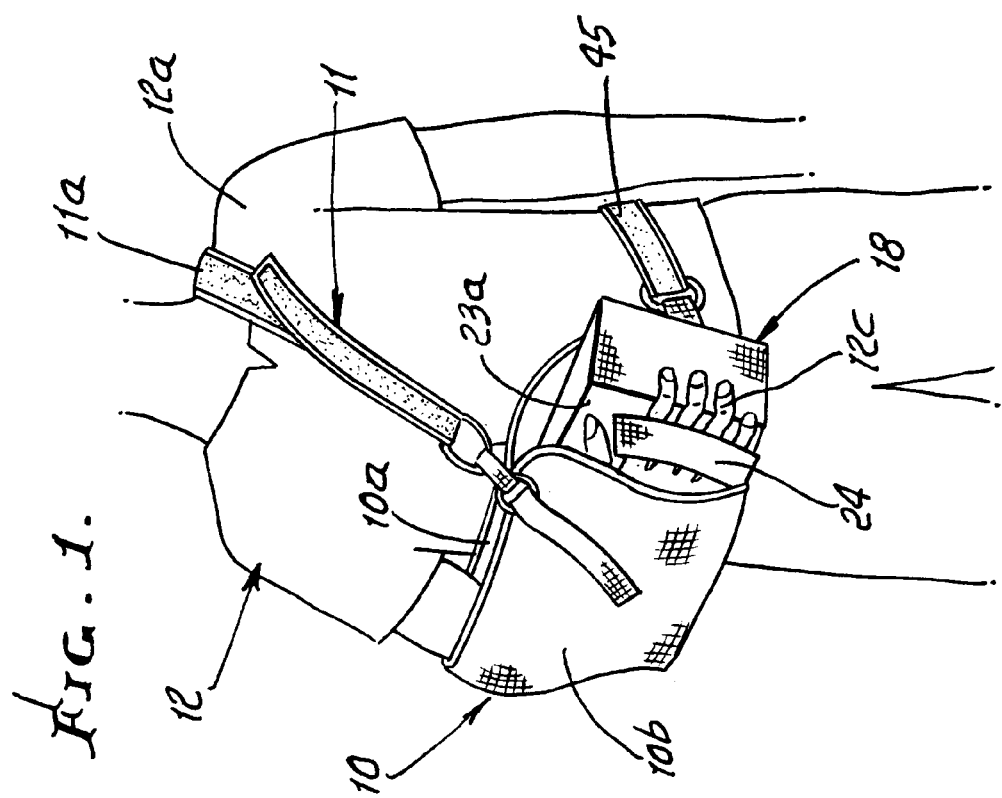

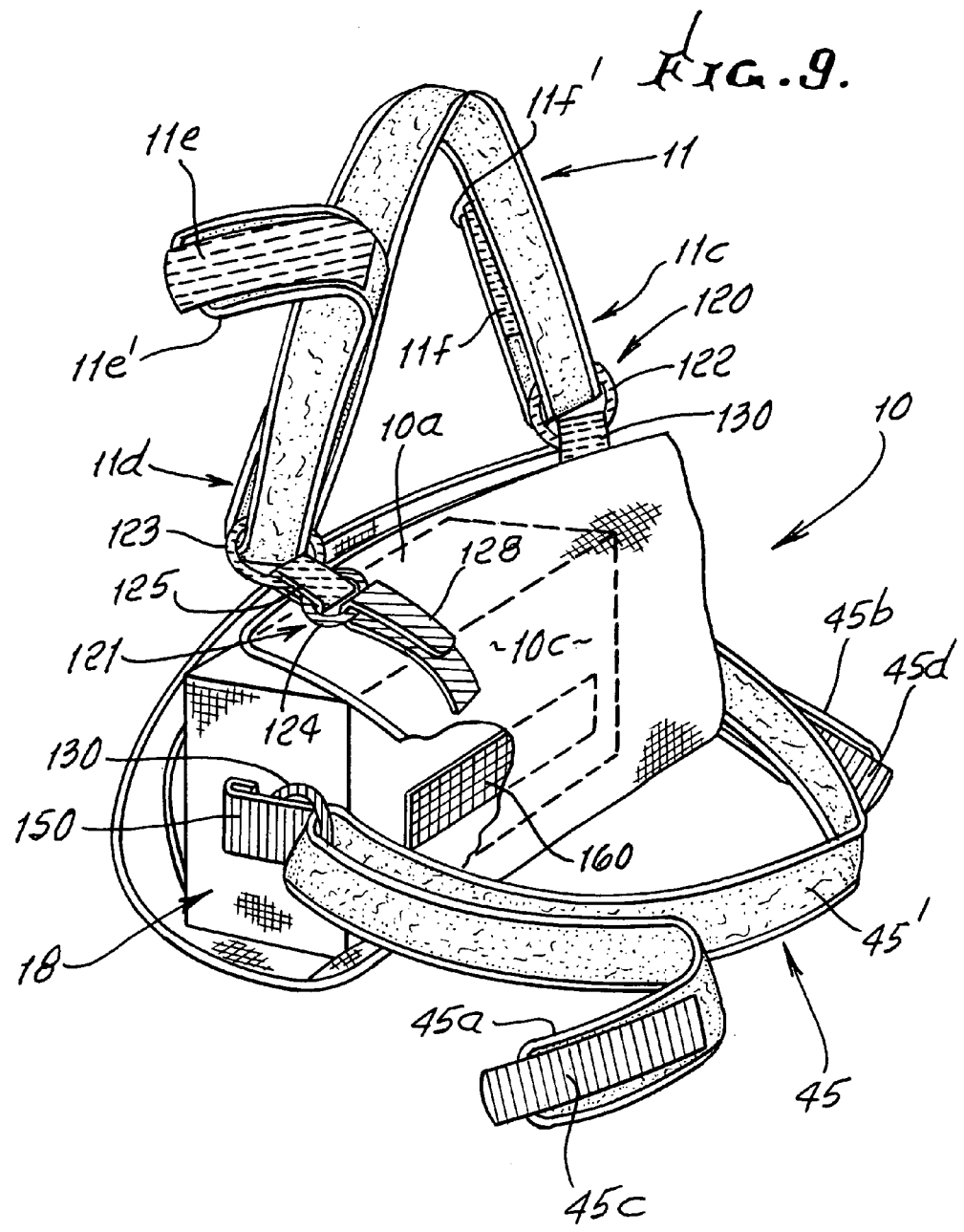

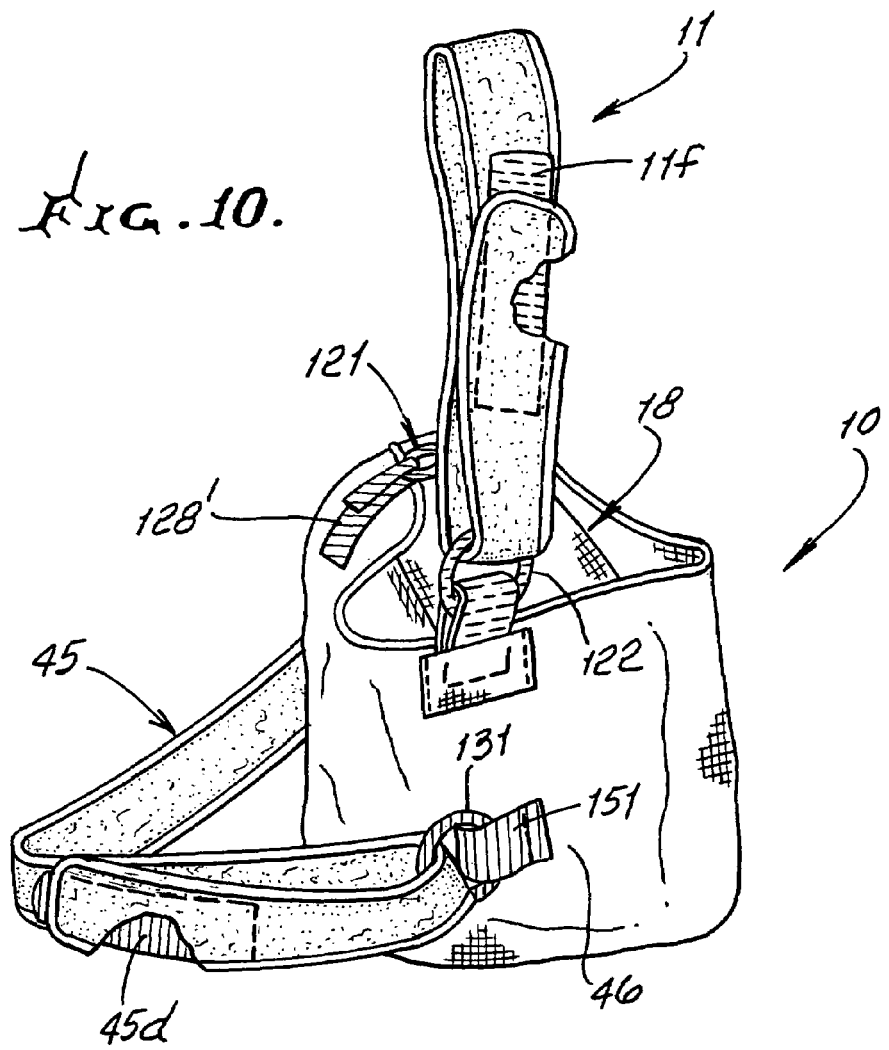
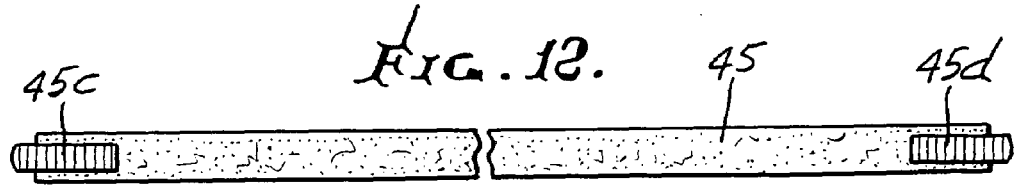

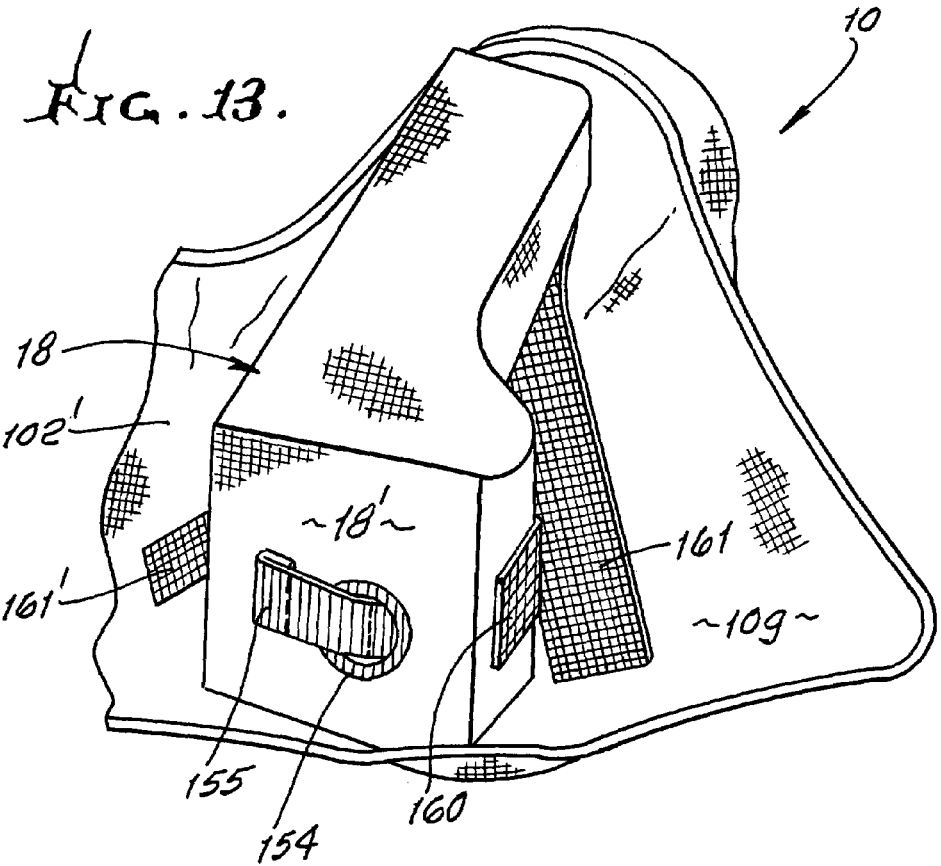
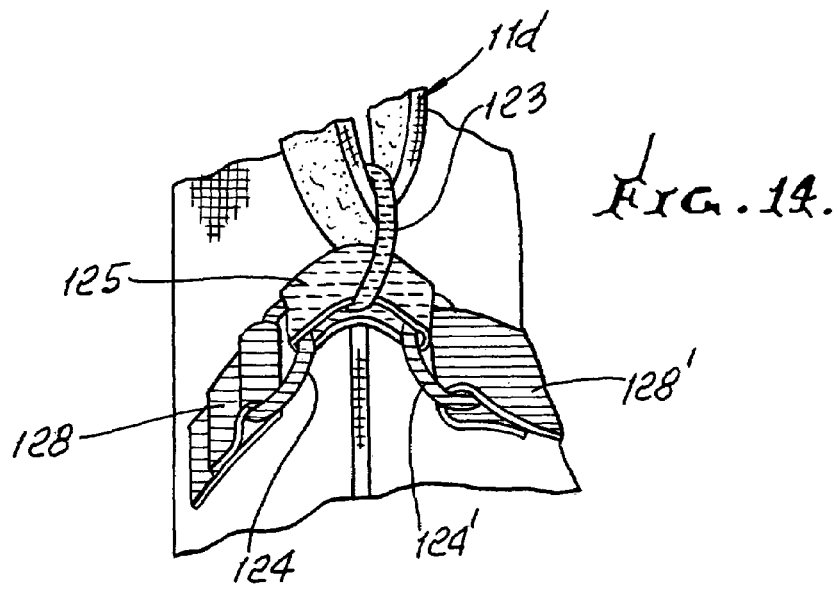

ARM SUPPORT IN SLING, WITH CODED STRAP AND/OR CONNECTIONS

This application is a continuation-in-part of prior U.S. application Ser. No. 10/718,058, filed Nov. 21, 2003 now U.S. Pat. No. 7,189,213.

BACKGROUND OF THE INVENTION

This invention relates generally to human arm supports, and more particularly to comfortably supporting that forearm in an immobile position, spaced from the torso.

There is need for such arm supporting device, and particularly after surgery, and when a patient is bedridden. In particular, there is need for a simple, effective, arm support that is easily applied with minimum disturbance to the arm itself, and with coded straps and/or pillow connection facilitating ease and rapidity of correct application to the user's arm.

SUMMARY OF THE INVENTION

It is a major object of the invention to provide an improved arm support apparatus meeting the above need. Basically the invention is embodied in a sling apparatus that comprises, in combination:

a) a flexible sling, with a first strap having connection to the sling, to be supported by a user's shoulder area, b) an insert pillow received in the sling, and to be retrievable from the sling, c) the sling and pillow dimensioned to receive a user's forearm alongside the pillow, in the sling, there being a second strap having connection to the sling and pillow for holding the sling and pillow proximate the user's body, said first strap connection having color A and said second strap connection having color B.

As will be seen, the pillow typically has a width between 2½ and 5 inches, to support the forearm at that distance from the human torso to which the sling is applied, the pillow extending forwardly, along side the forearm and held in that position by the sling. Also, the pillow preferably consists of foam material, and has a jacket covering the foam material, and may have releasable connection to the sling for positioning.

It is another object of the invention to provide a sling having forwardly extending panels which are foldable to be connectible together along upper extent of the sling, to close the sling over the user's forearm and pillow, and to allow upward opening of the sling to release the user's forearm and the pillow.

Yet another object is to provide a strap that extends about the user's body and has opposite ends respectively connected to the sling and to the pillow, and having length to extend about the user's body.

A further object is to provide a sling having a releasable drop panel which, when dropped, allows the user's forearm to dangle downwardly from and below the sling. A user's hand holder associated with the pillow is manipulable to release the hand and arm, to hang downwardly as described.

An added object is to provide a sling having a bottom panel which is adjustable in width to allow sling size adjustment. Such sling size adjustment easily accommodates to different size (width) arms to be retained against the side of the pillow by the sling, so that only one size pillow is needed, but multiple sizes are accommodated.

Additional objects include provision of strap structure incorporating elongated body strap structure having connection to the pillow proximate one end of the sling, and also having connection to the opposite end of the sling. The connection or connections typically include elements with adjustable connections to the strap structure. The strap structure typically includes strap terminal portions with VELCRO connection to intermediate extent of the strap structure, proximate a side of the sling. Such terminal portions extend toward one another, and said strap terminal portions and said elements all have color A.

Further objects include provision of a sling support strap that has end connections at opposite ends of the sling. Such connections typically include loops having color B; and there may be two of said loops at said side of the sling, of color B, and either or both of said two loops is or are connected to the support strap, via an auxiliary VELCRO strap.

An additional object includes provision of d) a body strap having connection of color B to the sling and pillow; and e) a support strap having connection of color A to the sling, at spaced locations.

The pillow may have VELCRO connection to the sling at multiple locations C. Such A, B and C color coding of connections facilitates ease and rapidity of assembly, use and application of the device, as will be seen.

The novel sling and pillow apparatus therefore has many advantages as well as multiple modes of operation, all embodied within a single, effective, easily applied and removed apparatus, particularly as respects bedridden patients.

These and other objects and advantages of the invention, as well as the details of an illustrative embodiment, will be more fully understood from the following specification and drawings, in which:

DRAWING DESCRIPTION

FIGS. 1 and 2 are frontal and rearward perspective views of preferred apparatus embodying one form of the invention;

FIG. 9 is a perspective view showing another form of the invention, with color coded connections;

FIG. 10 is a rear elevation of the FIG. 9 apparatus;

FIGS. 11 and 12 are views showing color coding of sub-straps in the FIGS. 9 and 10 apparatus;

FIG. 13 is a view showing internal color coding of structure; and

FIG. 14 is a fragmentary view showing color coding of strap connection structure.

DETAILED DESCRIPTION

Figure 3:
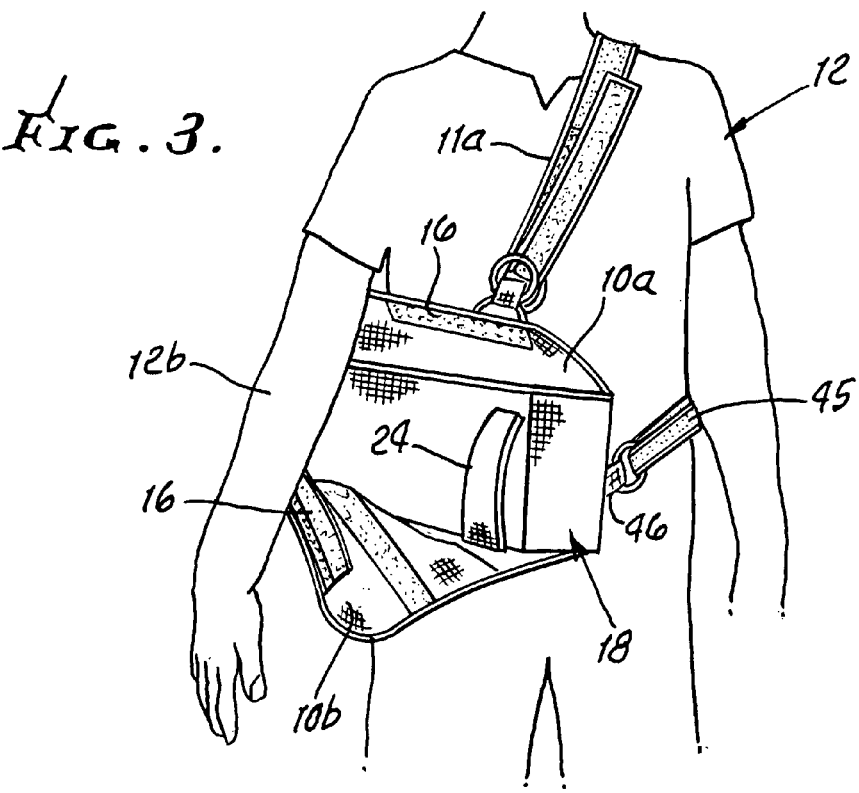
FIG. 3 is a view like FIG. 1 but showing sling panels separated away from a pillow retained in the sling.

In the drawings, a flexible sling 10 has a strap 11 to be supported by a user's shoulder area 12a, so that the strap extends at 11a at the front of the user's body 12, and at 11b at the rear of the body.

Figure 7:
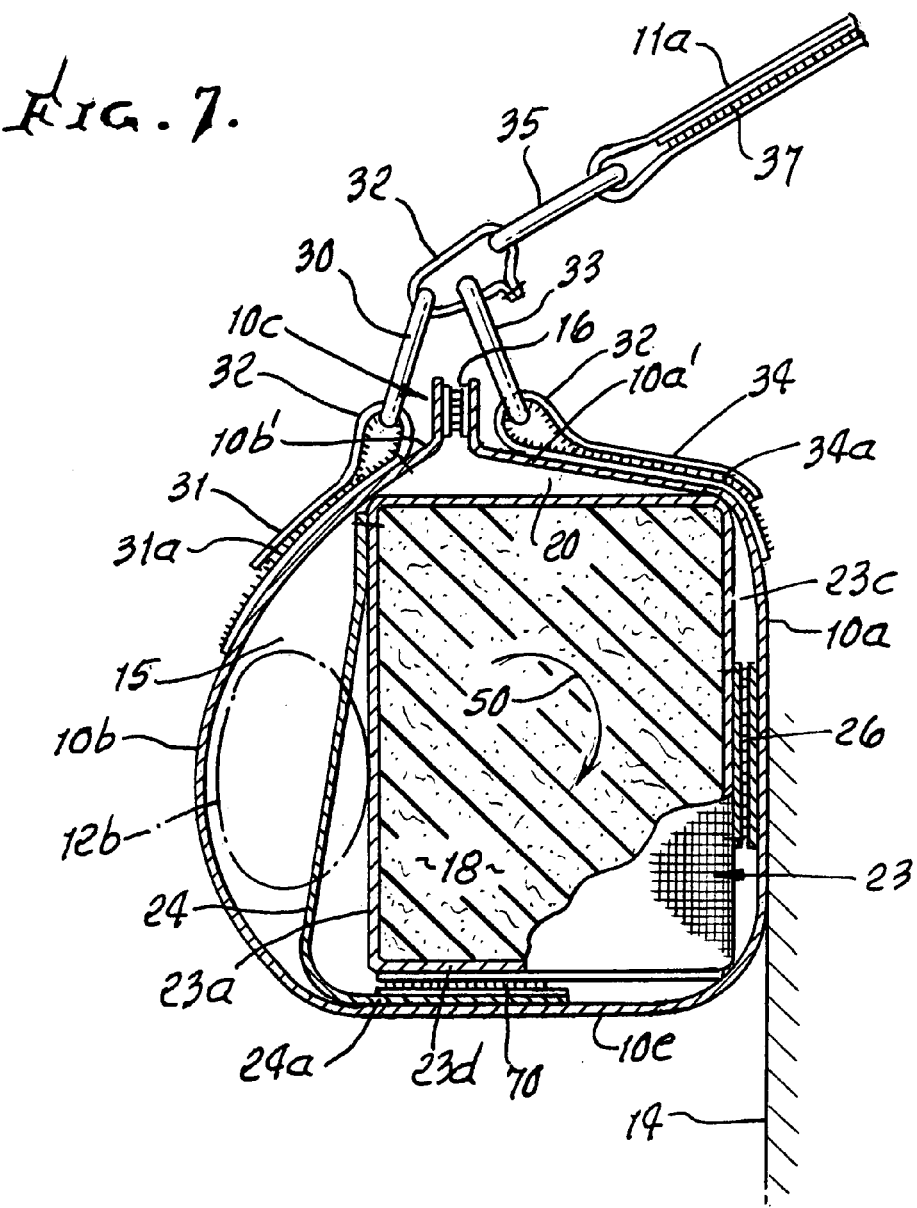
FIG. 7 is a section taken in elevation on lines 7-7 of FIG. 6.

The sling has spaced apart, forwardly extending panels 10a and 10, which are foldable to be connected together along upper extent 10c of the sling, as for example is shown in FIG. 7. Panel 10a is an inner panel positioned to rest against the user's side 14; and panel 10b is an outer panel positioned to extend as shown, adjacent the user's arm 12b in space 15. A connection is shown at 16 for interconnecting upper extents of the panels, in a forward and rearward direction 17. That connection may for example comprise hook and pile elements, as shown, enabling ready release of the connection 16.

Figure 5:
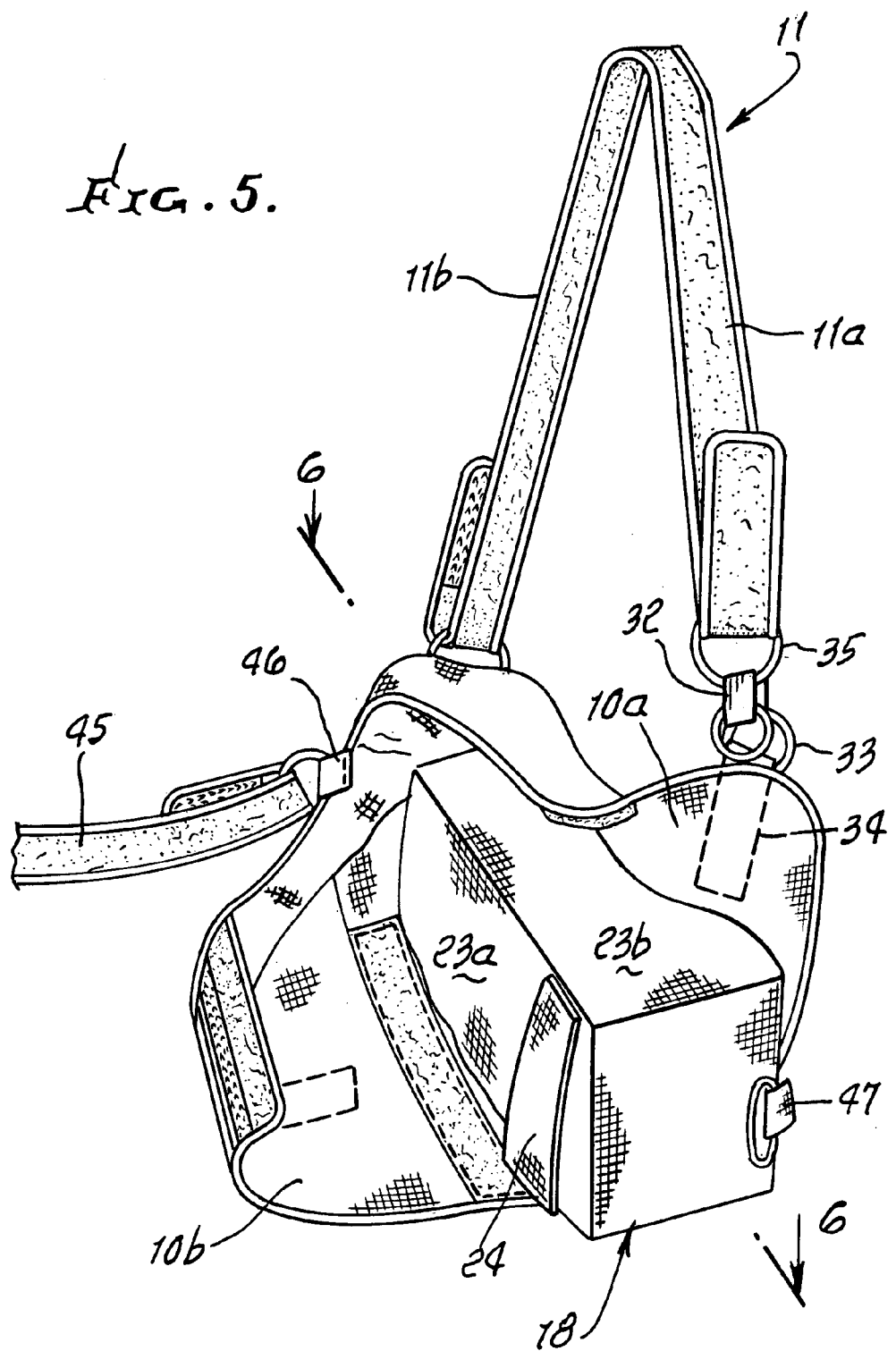
FIG. 5 is a more detailed view, taken in frontal perspective, showing the opened sling, and pillow.
Figure 6:
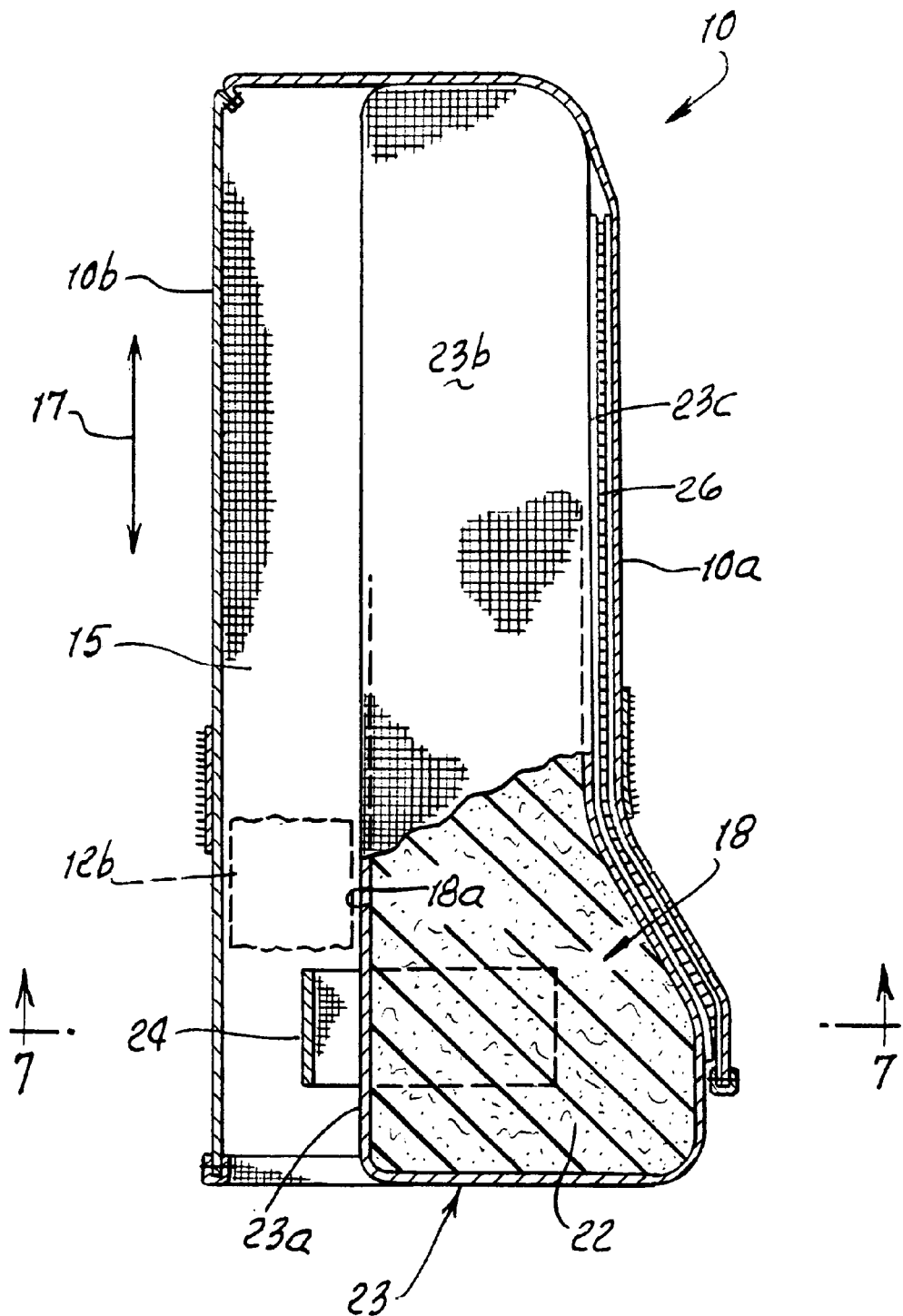
FIG. 6 is a plan view taken in section on lines 6-6 of FIG. 5.

An insert pillow 18 is received into the sling, as for example downwardly when connection 16 is opened as seen in FIG. 5. The received pillow is located in space 20, between arm space 15 and panel 10a, whereby the pillow comfortably holds the user's arm 12b in outwardly spaced relation to the user's side 14, the tensioned sling panel 10b holding the user's arm against the pillow side 18a. The pillow may consist of yieldably compressible pad material 22 such as foam rubber, or foam plastic, and a jacket 23 surrounding the pad, as at 23a-23d, in FIG. 7. A finger or hand retention strap 24 extends adjacent the forward end of the pillow at its side facing space 15. The strap lower end 24a has VELCRO connection to the pillow, bottom panel 10e as at 70.

The pillow itself preferably has adjustable VELCRO connection to the sling, as at connection 26 to sling panel 10a, to adjustably position the pillow in the sling, for most comfort to the user's arm 12b.

Sling strap 11a has connection to upper portions 10a' and 10b' of both sling panels 10a and 10b, as seen in FIG. 7. See ring 30 connecting adjustable strap 31 to loop 32; and see ring 33 connecting adjustable strap 31 to loop 32. Ring 35 connects loop 32 to sling shoulder strap 11a, as shown. VELCRO connections 31a and 34a allow length adjustment of folded-back straps 31 and 34 whereby rotary positioning (see arrow 50) of the pillow in the sling can be achieved; and VELCRO connection 37 allows length adjustment of sling strap 11b.

Figure 4:
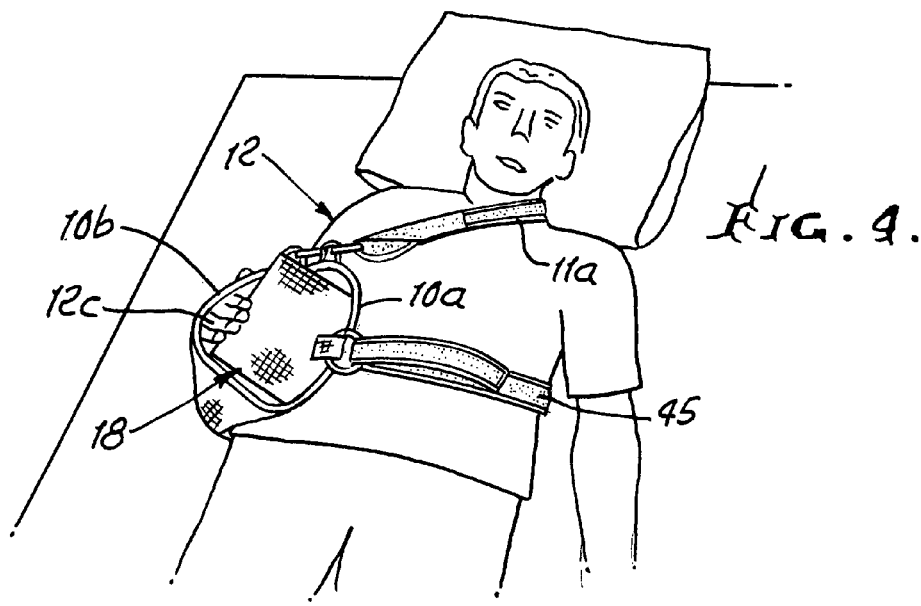
FIG. 4 is a view of a bedridden patient to which the sling apparatus and pillow are easily applied, as for example by pillow insertion into the opened sling.

When strap 31 is disconnected from panel 10b, outer sling panel 10b can be dropped, after release of the connection 16. This allows alternative downward flexing and positioning of the user's arm 12b, as to a hanging condition, as seen in FIG. 3, below the level of the sling panel 10b, as for arm medical or other treatment, without requiring removal of the pillow 18 from the sling. Thereafter, the user's forearm 12b can be flexed up at the elbow and re-positioned adjacent the pillow side as in FIG. 7, and the panel 10b re-attached at 16 to panel 10a, and strap 31 re-attached to loop 32. These steps can be easily accomplished while the user is in lying or reclining position, as in a medical facility as seen in FIG. 4, without disturbing the sling straps 10a and 10b, or a body retention strap 45. The latter has attachment to the sling at 46, as seen in FIG. 2, and to the pillow at 47 as seen in FIG. 5. These connections assure positioning of the pillow in the sling, during use and adjustment. The user's hand 12c is shown in FIG. 1, retained to the pillow by strap 24.

Figure 8:
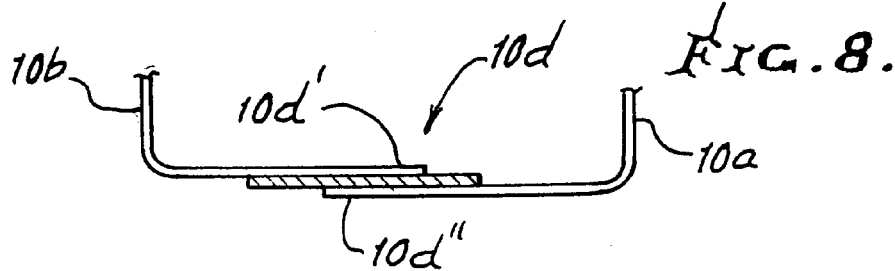
FIG. 8 is a vertical section showing a modification.

FIG. 8 shows an optional sling bottom panel 10d which is adjustable in width between side panels 10a and 10b. See overlapping sections 10d' and 10d'' of panel 10d, VELCRO connected to allow width adjustment of 10d, below the pillow.

The pillow width is typically between 2½ and 6 inches. The pillow may consist of an inflatable container, rather than foam rubber of foam plastic. The pillow may be removed or omitted, enabling use of the device in another arm sling mode.

In FIG. 9, the strap structure includes a sling support strap 11 having one strap end 11c connected to one end of the flexible sling 10 as via connection at 120. The strap has an opposite end 11d connected to a side 10a of the sling, as via connection structure 121. Connection 120 includes a loop such as ring 122, and connection structure 121 includes loops such as rings 123 and 124. The loops typically have colored surfaces, as for example matching colors B (such as white) surfaces on rings 122 and 123 that engage the strap ends or terminals. Those engaged strap terminals may have connections, such as adjustable length VELCRO connections of side facing color B, indicated as white in FIG. 9 at strap side locations 11e and 11f. Ring 124 has color C, as for example blue. It is connected to ring 123 by a short strap 125 of color B (white), and it is connected to the sling side 10c by a short adjustable length strap 128, of color C, i.e. blue. Ring 122 is connected to the sling as by short strap 130, of color B (white). See also ring 124', and strap 128' at the upper opposite side of the sling, in FIG. 14.

In addition strap ends 11c and 11d are lengthwise adjustable, as by looping through rings 122 and 123 and shiftable relative to those rings. Strap end extents 11e' and 11f'' are typically VELCRO connected to strap medial extent 11q. White colored end locations 11e and 11f may consist of white fabric adhered to strap end extents 11e' and 11f''. The white coloring of the rings 122 and 123 indicates that the white colored ends, at 11e and 11f of the strap 11 are to be passed through those rings, facilitates rapid accurate assembly of the strap to the sling.

Body retention strap 45 has a medial portion 45' that fits through loops or rings 130 and 131 retained at opposite ends of the flexible strap. Strap end extents 45a and 45b have identifying side facing coloring D at 45c and 45d, as for example red, or associated colored fabric. This indicates to the user that strap end extents 45a and 45b are to be adjustably rapidly and accurately attached, as by VELCRO connections to exposed fabric on the strap material portion 45a, after strap end assembly passage through the rings 130 and 131, also having coloring D, as for example red, upon initial assembly of strap 45 to the sling opposite ends. Short straps 150 and 151, also bearing coloring D, operatively attach the rings 130 and 131 to the sling. In the example, short strap 150 connects ring 130 to the end wall of pillow 18, carried at the sling interior; and short strap 151 connects ring 131 to sling opposite end, at 46.

See also FIG. 13, showing a color D connection ring 154 attached by color D short strap 155 to the opposite end 18' of pillow 18, or for alternate connection of the strap 45 to that end of the pillow.

FIG. 11 schematically shows the white fabric at 11e and 11f on the extended strap 11; and FIG. 12 shows the red fabric at 45c and 45d on the extended strap 45.

Finally, FIG. 13 also shows colored matching fabric zones 160 and 161 at the sling interior, zone 160 located at the outer side wall 18b of pillow 18, and zone 161 located at the inner side wall 10q of the sling fabric. Zones 160 and 161 are of the matching color E, as for example yellow, and indicates where the pillow is to be located, in the sling, as by face to face assembly of those VELCRO zones. The zones may also provide VELCRO connection of the pillow to the sling.

Another yellow VELCRO fabric zone 161' may be provided at the inner side of the sling fabric wall 102', at the opposite side of the pillow, for connection to 160 if the pillow is reversed, to support the user's opposite arm. Zones 161 and 161' extend in generally parallel relation.

I claim:

1. An arm supporting pillow in sling apparatus, comprising in combination
   a) a flexible arm sling, with a first strap having connection to the sling, and to be supported by a user's shoulder area,
   b) an insert pillow received in the sling, and retrievable from the sling, the pillow having elongated block shape, and the sling and inner side of the pillow each having adjustable hook and loop configurations adapted for attachment of the pillow to the inner side of the sling,
   c) the sling and pillow dimensioned to receive a user's forearm alongside the pillow, in the sling,
   d) the sling having forwardly extending panels which are foldable to be connectable together along upper extent of the sling, spaced above the pillow, to close the sling over the user's forearm and pillow, and to allow upward opening of the sling to release the user's forearm and the pillow,
   e) there being a user's forearm receiving pocket formed between the pillow in the sling and outer extent of the sling facing inwardly toward the pillow, and defining one of said panels,
   f) elongated body strap structure having first connection to the pillow proximate one end of the sling, and also having second connection to the opposite end of the sling for holding the sling and pillow proximate the user's body, said first strap connection having color material of a first color and said second strap connection having material of a second color.

2. The combination of claim 1 wherein the pillow has a width between 2½ inch and 6 inches.

3. The combination of claim 1 wherein the first strap has releasable connection to the sling, proximate fore and aft ends thereof.

4. The combination of claim 1 wherein the sling has a releasable drop panel which, when dropped, allows the user's forearm to dangle downwardly from and below the sling.

5. The combination of claim 4 wherein the drop panel, when released, dangles downwardly from a rear portion of the sling while remaining carried by the sling.

6. The combination of claim 1 including a hand holder carried adjacent a fore portion of the pillow.

7. The combination of claim 6 wherein the hand holder comprises a strap, adjustably attached to the pillow.

8. The combination of claim 1 wherein the pillow consists of foam material, and has a jacket covering the foam material.

9. The combination of claim 8 wherein said pillow consists of one of the following:
   i) foam rubber,
   ii) foam plastic,
   iii) an inflatable container.

10. The combination of claim 1 including a body strap having opposite ends with respective colored connections to the sling and to the pillow, and having length to extend about the user's body.

11. The combination of claim 1 wherein the pillow has releasable connection to the sling.

12. The combination of claim 1 wherein said connections include elements with adjustable connections to the strap structure.

13. The combination of claim 12 wherein said strap structure includes strap terminal portions with hook and loop connection to intermediate extent of the strap structure, proximate a side of the sling.

14. The combination of claim 13 wherein said strap terminal portions extend toward one another, and said strap terminal portions and said elements all have color A.

15. The combination of claim 1 including
   g) a body strap having connection of said second color to the sling and pillow; and
   h) a support strap having connection of said first color to the sling, at spaced locations.

16. The combination of claim 15 wherein said multiple locations extend in two rows, for alternate selection using one for left arm pillow support, and the other for right arm pillow support.

17. The combination of claim 15 including
   g) a pillow-to-sling connection or connections of third color.

18. The combination of claim 17 wherein said pillow and sling connections extend in two rows, for alternate selection using one for left arm pillow support, and the other for right arm pillow support.

19. The combination of claim 1 wherein said pillow has hook and pile connection to the sling at multiple locations, of a third color.

20. The combination of claim 19 wherein said colors, include red, blue and yellow connector material.

21. The combination of claim 19 wherein said colors, are on flexible connector material.

22. The combination of claim 1 wherein there are two of said connections respectively at opposite ends of a strap, said two connections respectively having two of said associated colors.

23. The combination of claim 22 wherein said colors are red and blue.

24. The combination of claim 22 wherein said colors are red and white.

25. The combination of claim 1 wherein
   g) there being an elongated holder strap for holding the container alongside a human body, there being third and fourth of said connections at opposite ends of said holder strap, said third and fourth connections having third and fourth of said associated colors.

26. The combination of claim 1 wherein said connections include loops having said second color.

27. The combination of claim 1 wherein said pillow has hook and loop connection to the sling at multiple locations, of third color.

28. An arm supporting pillow in sling apparatus, comprising in combination
   a) a flexible arm sling, with a first strap having connection to the sling, and to be supported by a user's shoulder area,
   b) an insert pillow received in the sling, and retrievable from the sling, the pillow having elongated block shape, and the sling and inner side of the pillow each having adjustable hook and loop configurations adapted for attachment of the pillow to the inner side of the sling,
   c) the sling and pillow dimensioned to receive a user's forearm alongside the pillow, in the sling,
   d) the sling having forwardly extending panels which are foldable to be connectable together along upper extent of the sling, spaced above the pillow, to close the sling over the user's forearm and pillow, and to allow upward opening of the sling to release the user's forearm and the pillow, e) there being a user's forearm receiving pocket formed between the pillow in the sling and outer extent of the sling facing inwardly toward the pillow, and defining one of said panels, f) elongated body strap structure having connection to the pillow proximate one end of the first sling, and also having second connection to the opposite end of the sling for holding the sling and pillow proximate the user's body, said first strap connection having material of a first color and said second strap connection having material of a second color, q) and wherein said connections include loops having said second color.

29. The combination of claim 28 wherein there are two of said loops at said side of the sling, of said second color, and either or both of said two loops is or are connected to a support strap, via an auxiliary strap.

* * * * *